United States Patent [19]

Turtel

[11] Patent Number: 6,080,169

[45] Date of Patent: Jun. 27, 2000

[54] STRABISMUS RECESSION CLAMP

[76] Inventor: Lawrence Turtel, 10 Matilda Dr., Wayside, N.J. 07712

[21] Appl. No.: 09/371,244

[22] Filed: Aug. 10, 1999

[51] Int. Cl.[7] .................................................. A61B 17/08
[52] U.S. Cl. .............................................................. 606/151
[58] Field of Search .................................... 606/151, 157, 606/158, 153, 152, 167, 205–210, 232, 233, 166, 172, 173

[56] References Cited

U.S. PATENT DOCUMENTS 848,126  3/1907  Roosevelt ................................ 606/157

*Primary Examiner*—Michael Buiz
*Assistant Examiner*—Hoa B. Trinh
*Attorney, Agent, or Firm*—Mandel & Peslk, LLC; Arthur M. Peslak, Esq.

[57] ABSTRACT

A clamp is meant to be used by eye surgeons during surgery to correct a condition known to lay persons as cross-eyes. The clamp is comprised of a solid first plate, a second plate comprising a longitudinal slit adapted to receive a knife blade, and a locking means for locking the eye muscle in place between the two clamps. The method for using the clamp during surgery is also disclosed.

3 Claims, 16 Drawing Sheets

$A_2 + B_2 = C_2$
A and B are known
2c - 2a = recession i.e. if 2a = 2mm and B is 3mm
$1^2 + 3^2 = 10$    $\sqrt{10} = 6.32$    6.32 - 2 = 4.32 mm recession

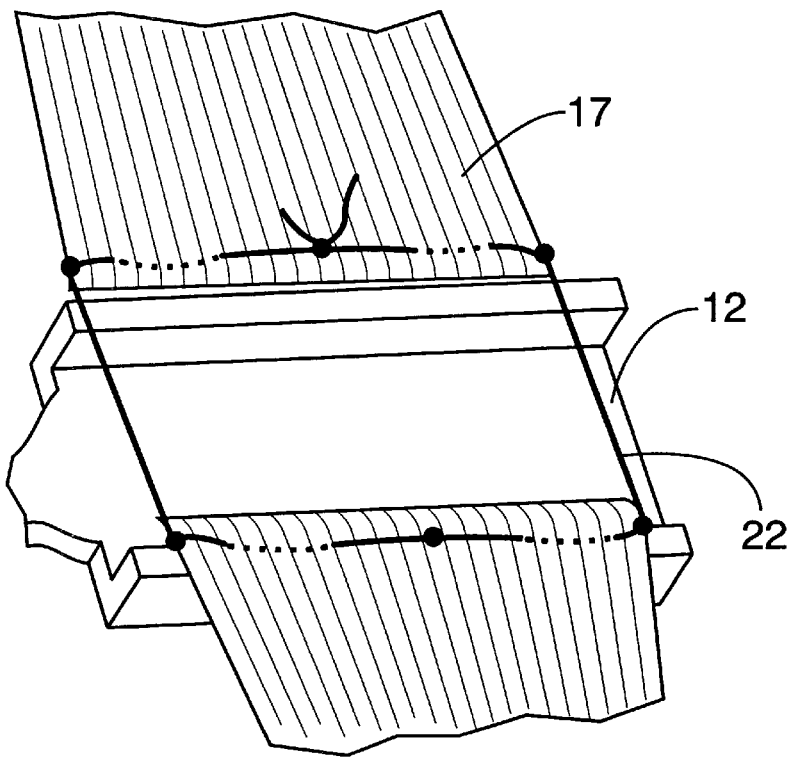
FIG. 9
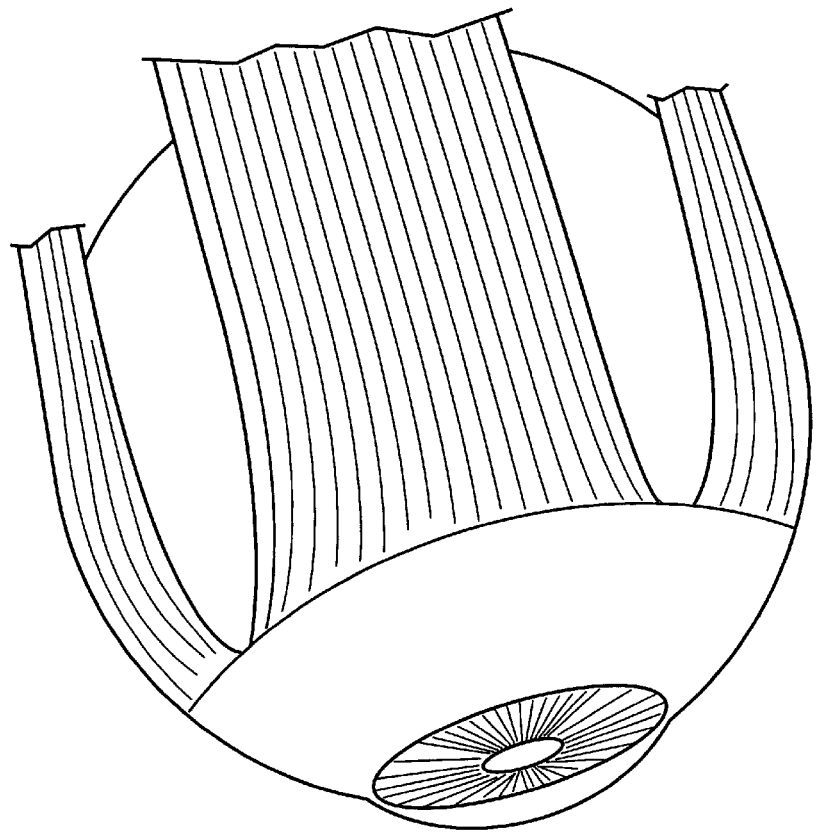

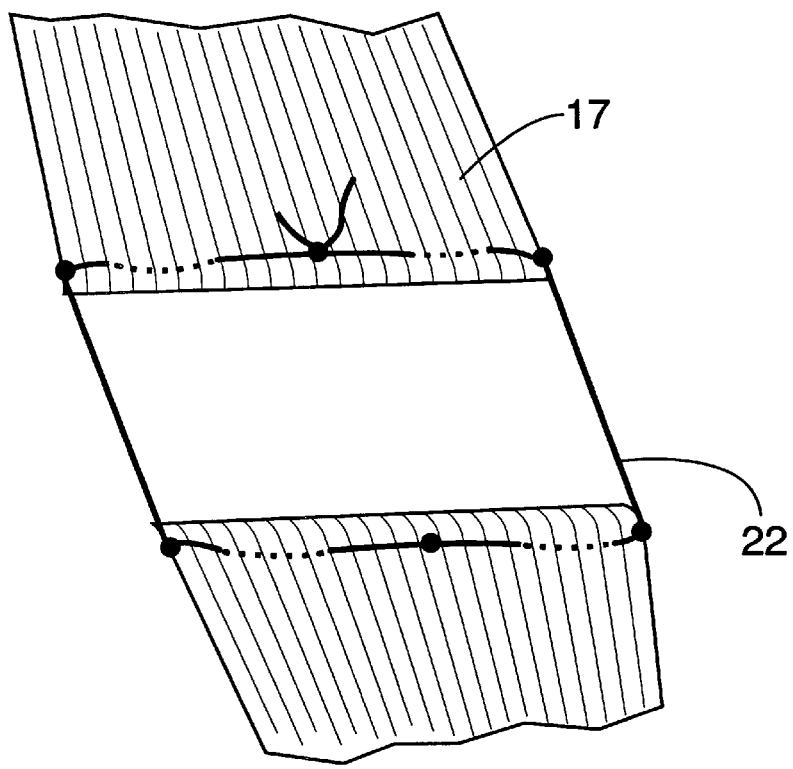
FIG. 10
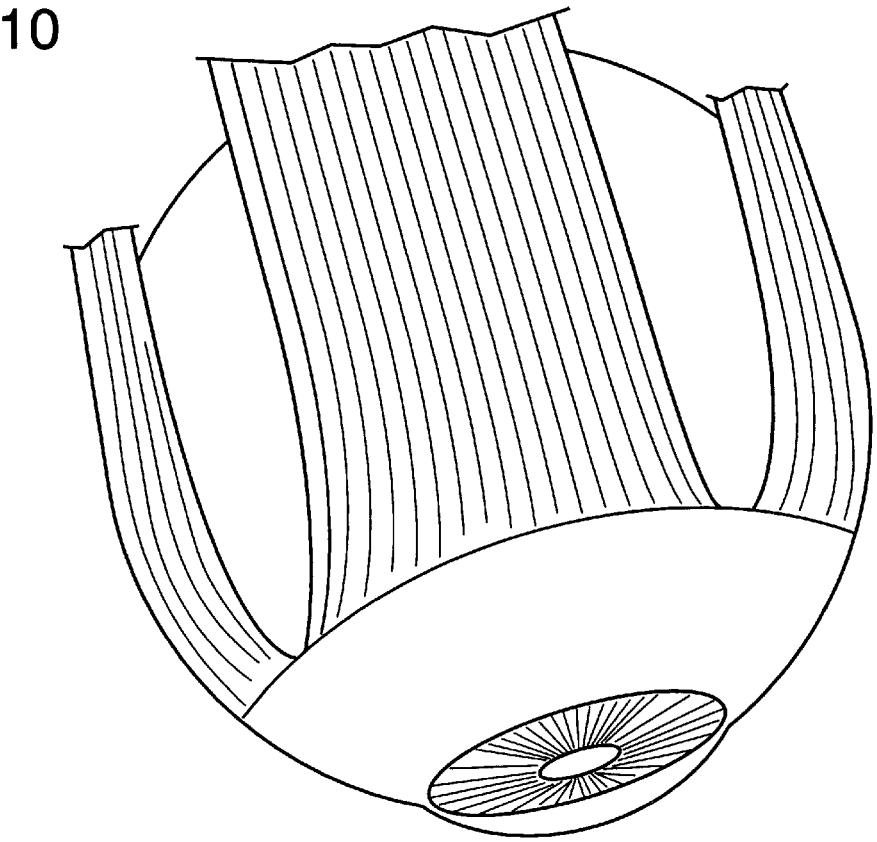

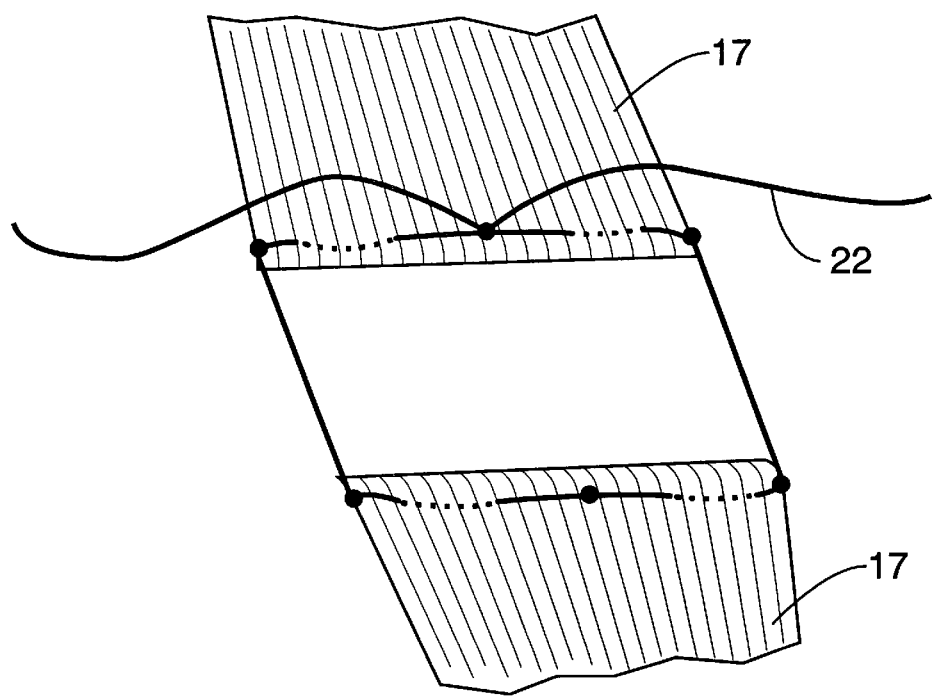
FIG. 11
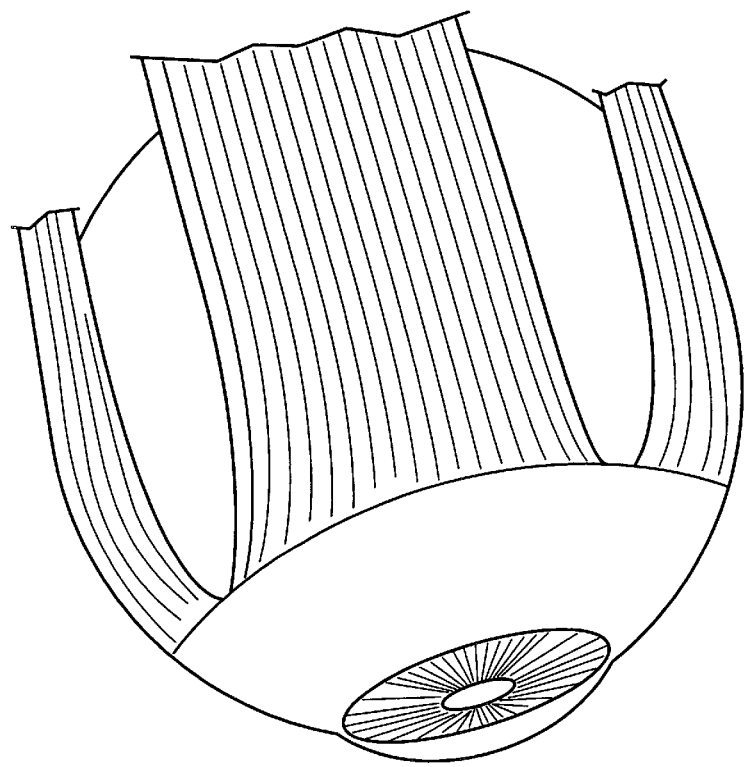

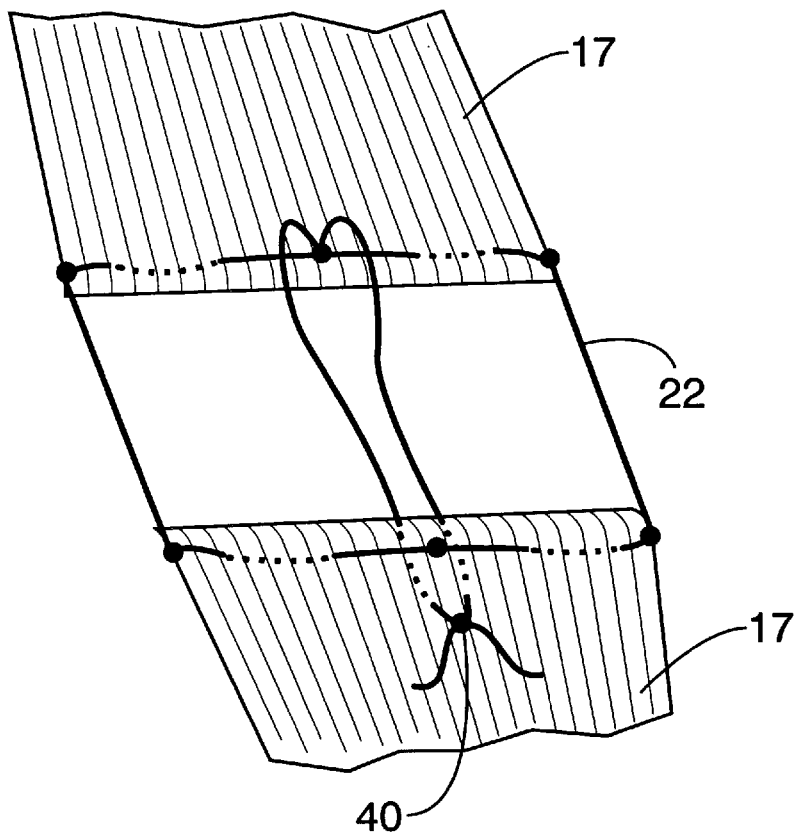
FIG. 12
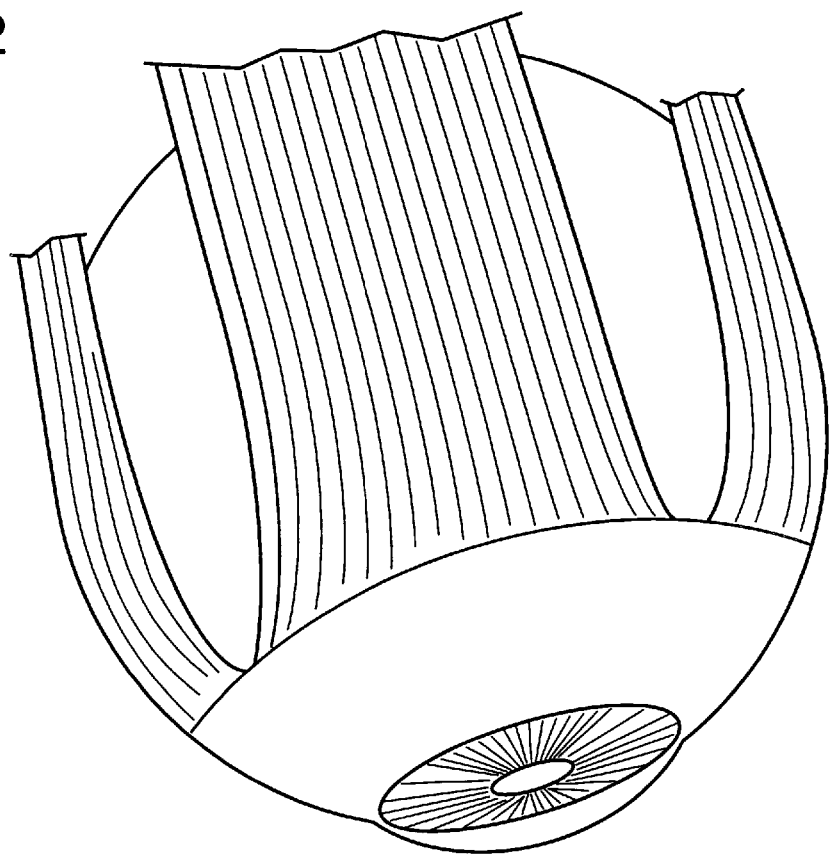

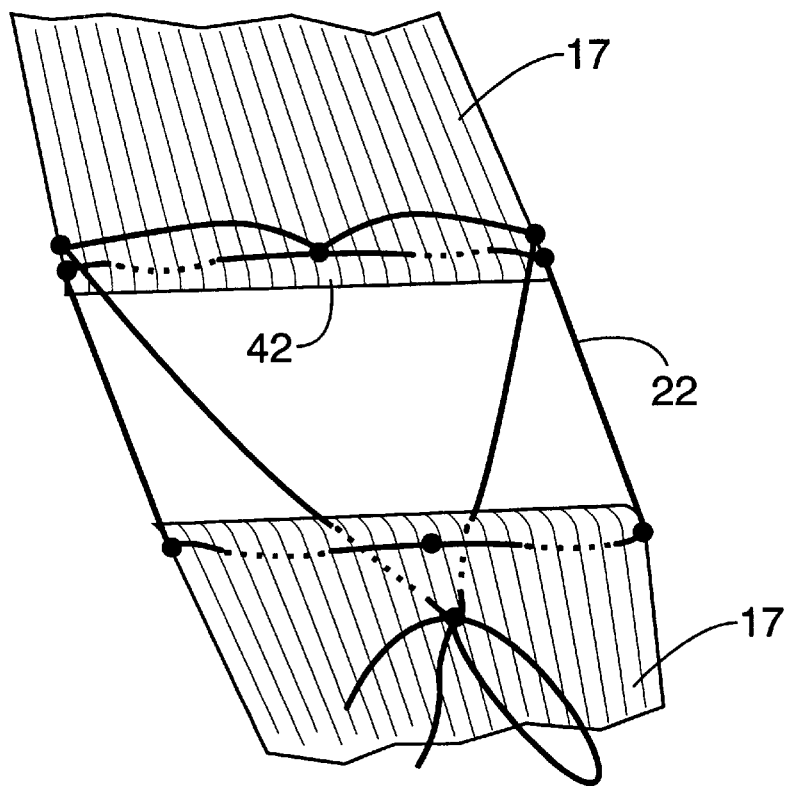
FIG. 13
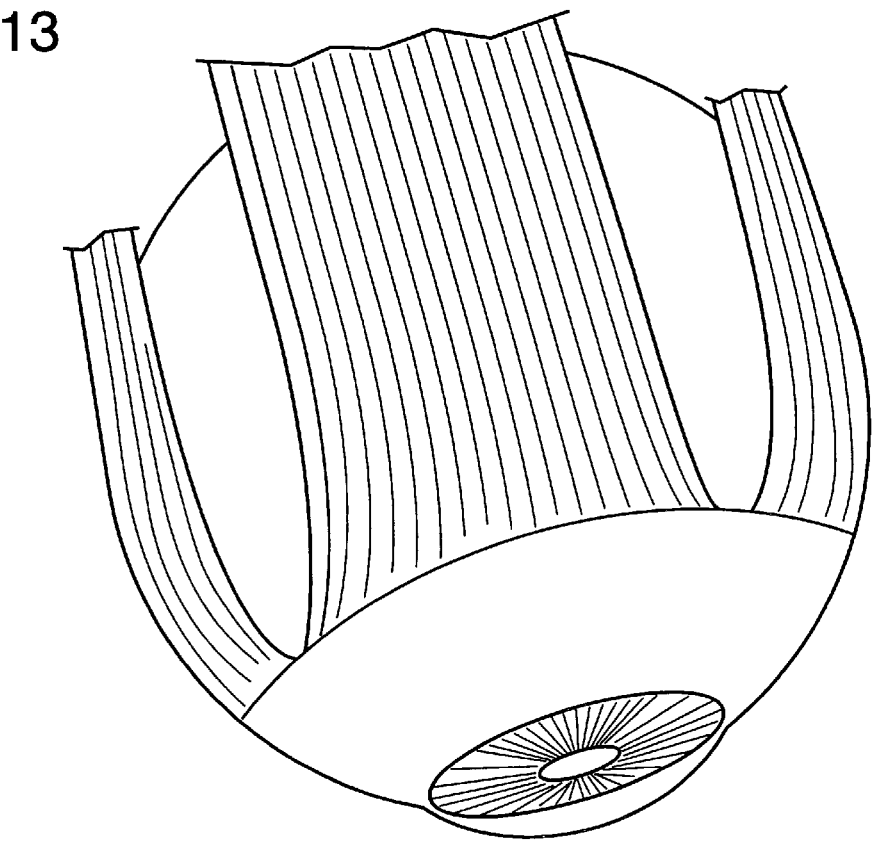

STRABISMUS RECESSION CLAMP

BACKGROUND OF THE INVENTION

The present invention is directed to the field of eye surgery. In particular, the present invention is directed to a clamp used in a procedure known as muscle recession surgery. This procedure is used to correct a condition known generally to lay persons as "cross-eyes."

During this procedure, a muscle located near the eye must be cut by the surgeon and then relocated to a different position. The prior devices used for this surgery are a muscle hook that is used to locate the muscle. Use of the prior devices entailed several risks including the risk of perforating the eye itself with a needle, locking forceps or scissors and the risk of intraocular infection that would be associated with an eye perforation.

The present invention provides a clamp that simplifies the surgical procedure and minimizes the risks associated with use of the prior devices and method. Among the advantages of use of the present invention is that the procedure is safer, takes less time to perform, the patient is under the effects of the anesthesia for a shorter period of time and is less expensive.

SUMMARY OF THE INVENTION

A strabismus recession clamp comprising a solid first plate comprising a top surface wherein the top surface is adapted to receive an eye muscle during a recession procedure, a second plate comprising a longitudinal slit wherein the longitudinal slit comprises hatch marks and is adapted to receive a knife blade during the recession procedure and the second plate is adapted to be received in the top surface of the first plate after the eye muscle is received in the top surface of the first plate and thereby a first groove for initial suturing of the eye muscle is formed between the first plate and the eye muscle and a second groove for recession of the eye muscle is formed between the first plate and the eye muscle, and a locking device for securing the second plate into position over the eye muscle after the second plate is received in the top surface of the first plate.

BRIEF DESCRIPTION OF THE DRAWINGS

FIG. 9 is another plan view of the embodiment of the present invention illustrated in FIG. 1 illustrating the use of the present invention.

FIG. 10 is a plan view illustrating a result of the use of the present invention illustrated in FIG. 1.

FIG. 11 is a plan view illustrating a result of the use of the present invention illustrated in FIG. 1.

FIG. 12 is a plan view illustrating a result of the use of the present invention illustrated in FIG. 1.

FIG. 13 is a plan view illustrating a result of the use of the present invention illustrated in FIG. 1.

DETAILED DESCRIPTION OF THE INVENTION

Figure 1:
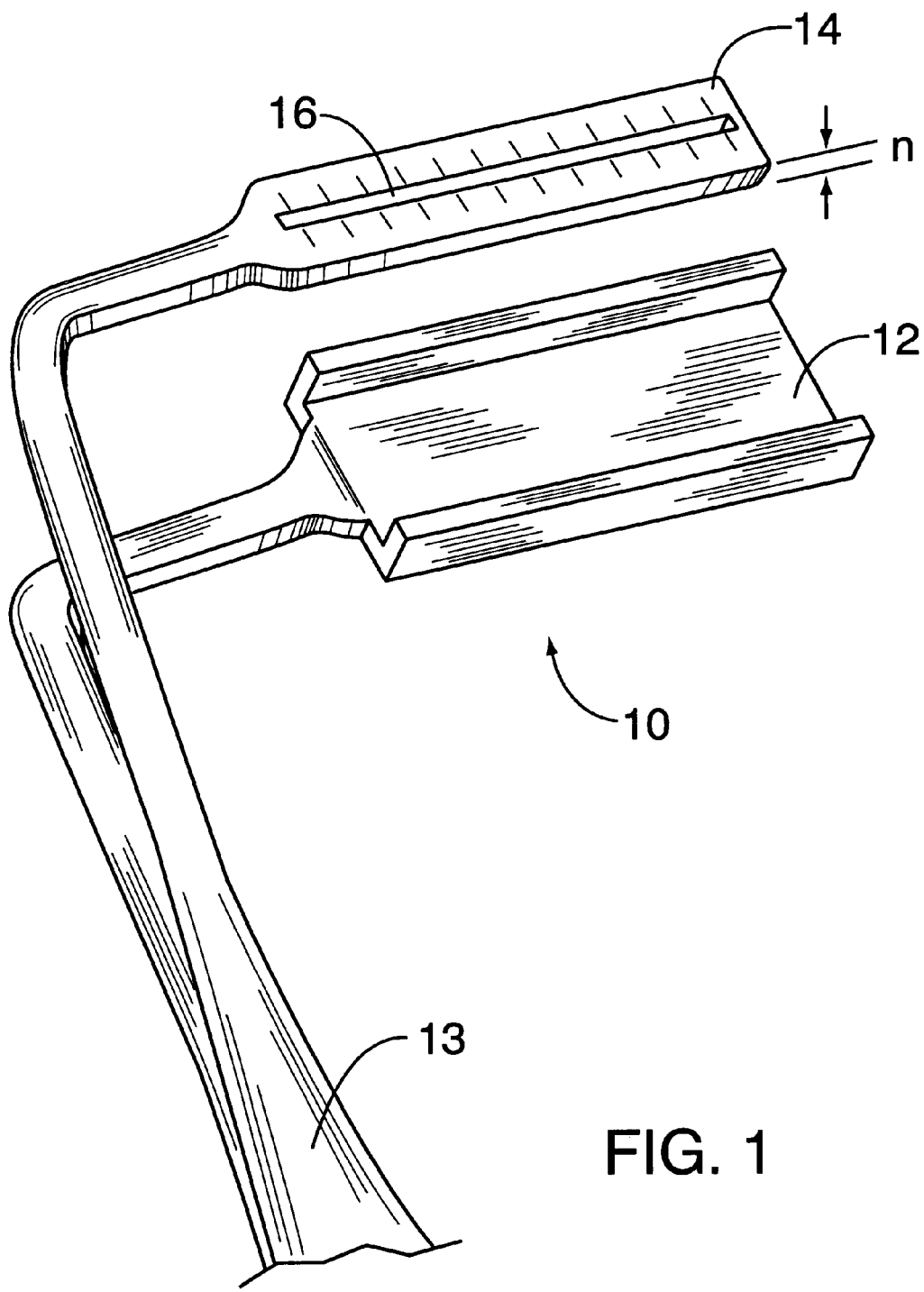
FIG. 1 is a plan view illustrating an embodiment of the present invention.

The present invention is directed to a Strabismus Recession Clamp 10. As shown in FIG. 1, the Clamp 10 is comprised of a first plate 12 and a second plate 14. The second plate 14 comprises a longitudinal slit 16 that runs through the entire thickness n of second plate 14.

Figure 2:
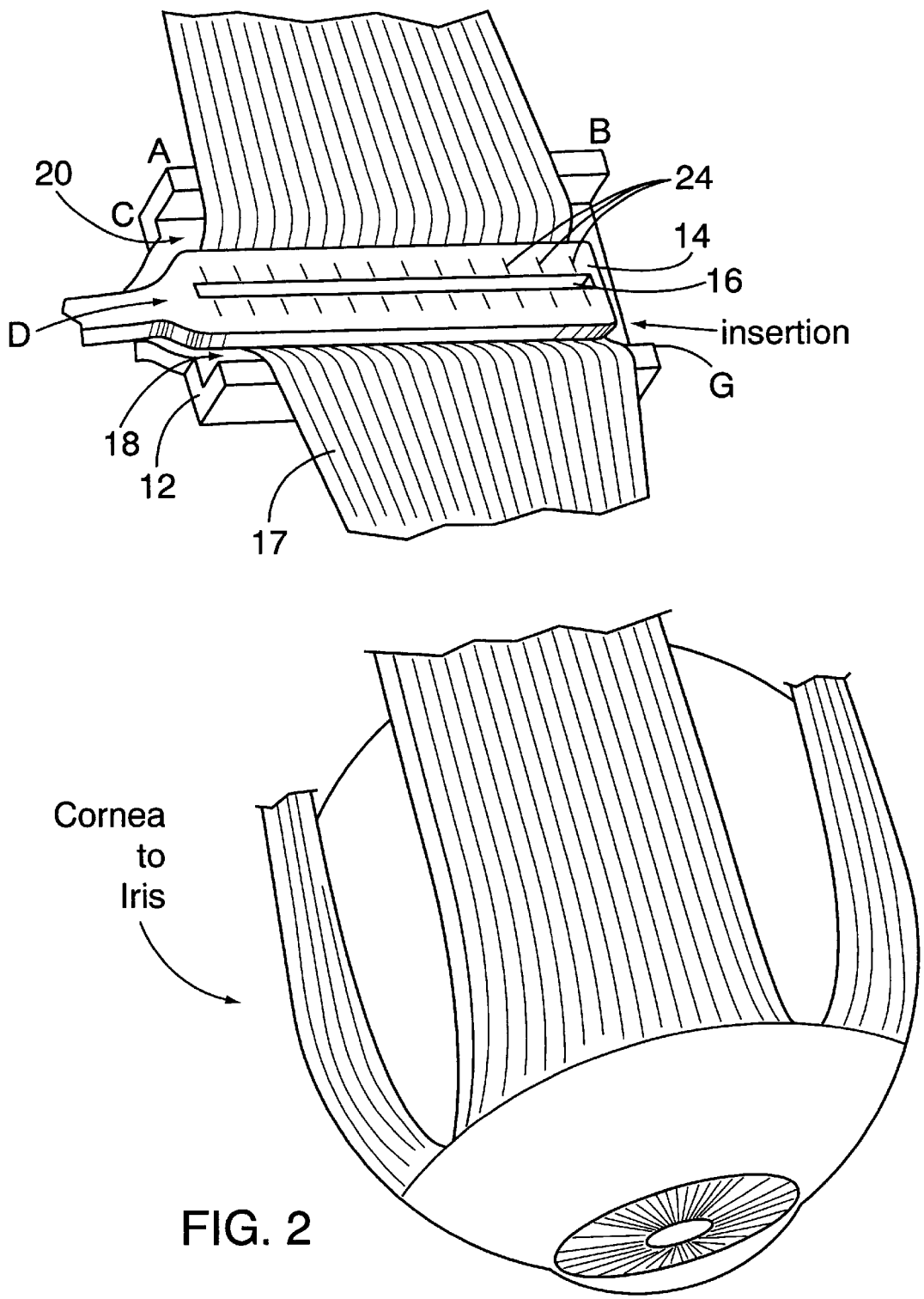
FIG. 2 is a plan view of the embodiment of the present invention illustrated in FIG. 1 illustrating the use of the present invention.

FIG. 2 illustrates the Clamp 10 as it is intended to be used. The first plate 12 replaces the traditional muscle hook used previously in connection with muscle recession surgery. The first plate 12 will be placed between the muscle 17 shown in FIG. 2 and the sclera. The second plate 14 will be placed above the muscle 17. A locking device of the type well known to those of ordinary skill in the art will be incorporated on the handle 13 of the Clamp 10 to allow the first plate 12 and the second plate 14 to be secure on the muscle 17 during the entire procedure.

It is anticipated that the Clamp 10 will also provide further advantages over the prior devices and methods. As is known to those of ordinary skill in the art, the prior methods require the use of traction sutures and locking forceps during the procedure to position the operative site. The Clamp 10 should suffice to position the operative site without the need for these devices. In addition, the Clamp 10 will provide for hemostasis during the procedure.

As shown in FIG. 2, the Clamp 10 holds the muscle 17 in place between first plate 12 and second plate 14. When the muscle 17 is clamped in place, two grooves 18 and 20 are created between the muscle 17 and first plate 12. The grooves 18 and 20 allow for the muscle 17 to be sutured while the sclera which is located under the first plate 12 is protected from accidental perforation when the sutures are placed in the muscle 17 as part of the procedure. The longitudinal slit 16 is adapted to receive a sharp knife tip for cutting the muscle 17 as more fully explained below. However, the first plate 12 protects the sclera from being accidentally perforated by the sharp knife during the cutting of the muscle 17. Second plate 14 is also provided with a plurality of hatch marks 21 along the length of slit 16 to measure the length of the muscle recession.

Figure 3:
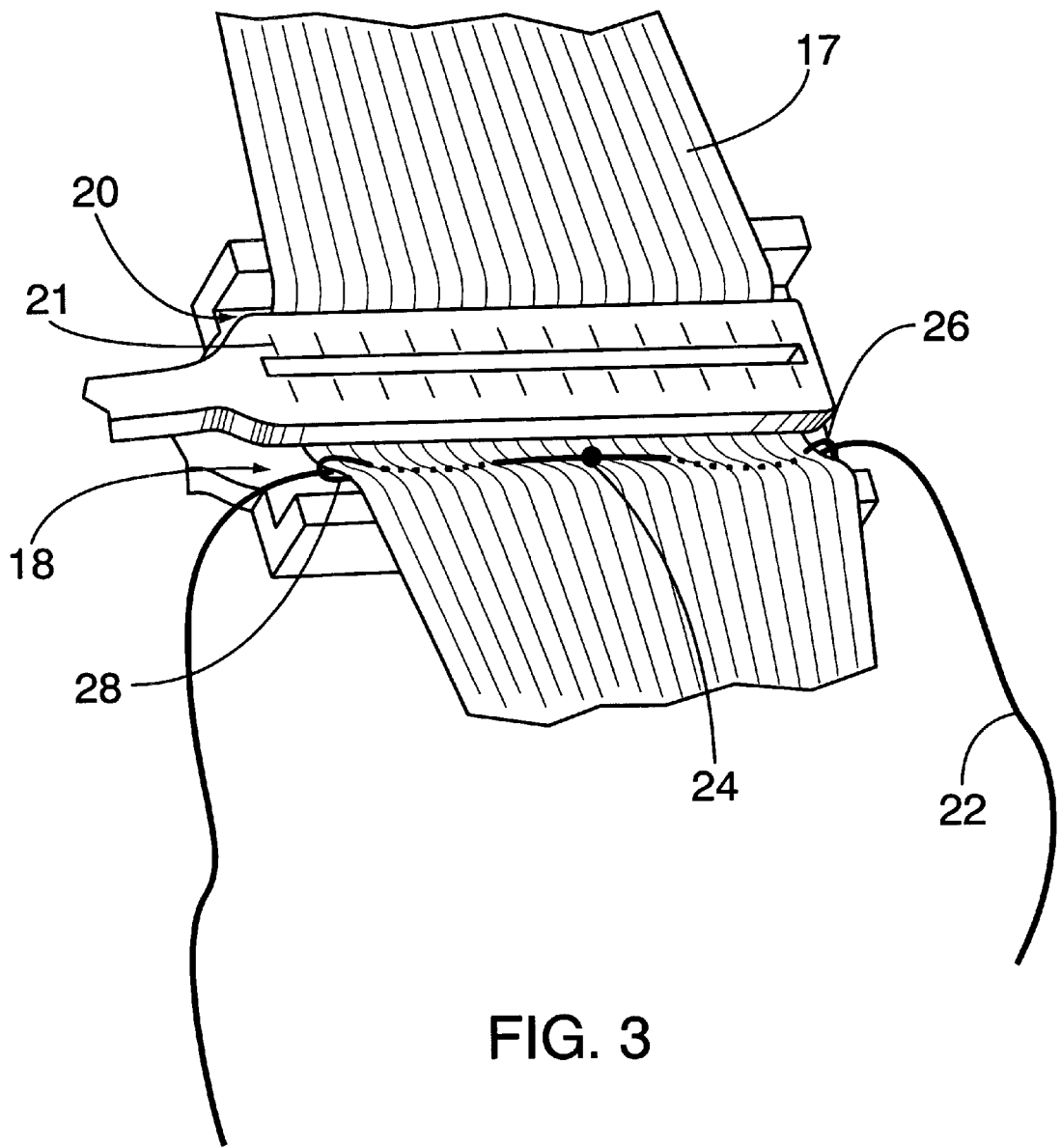
FIG. 3 is another plan view of the embodiment of the present invention illustrated in FIG. 1 illustrating the use of the present invention.

As shown in FIG. 3, the muscle 17 is initially sutured through groove 18. Groove 20 could alternatively be used for this initially suturing but the preferred method is through groove 18. This initial suturing is accomplished by threading a double-armed vicryl suture 22 through groove 18. A central knot 24 is placed in the suture 22 as well as locking bites 26 and 28.

Figure 4:
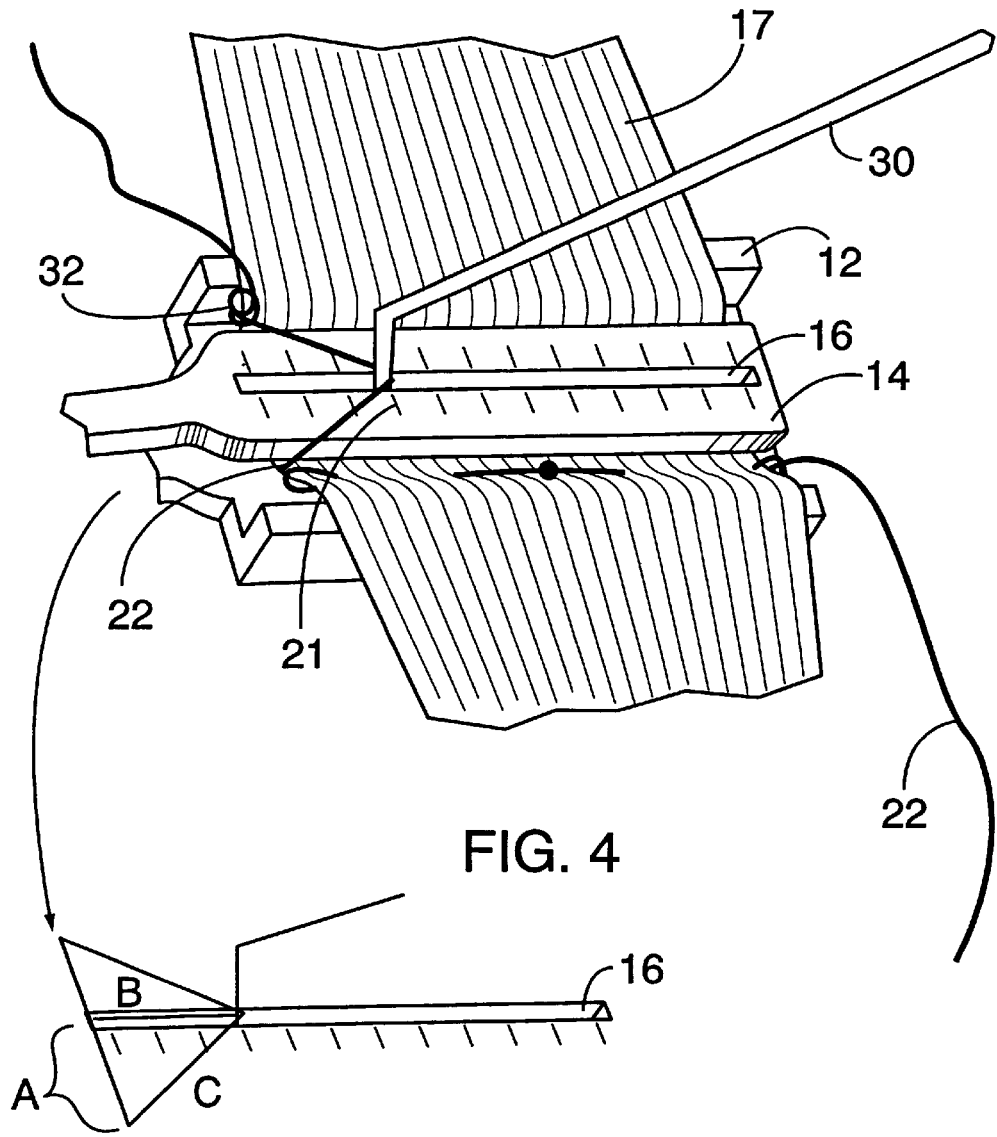
FIG. 4 is another plan view of the embodiment of the present invention illustrated in FIG. 1 illustrating the use of the present invention.
Figure 5:
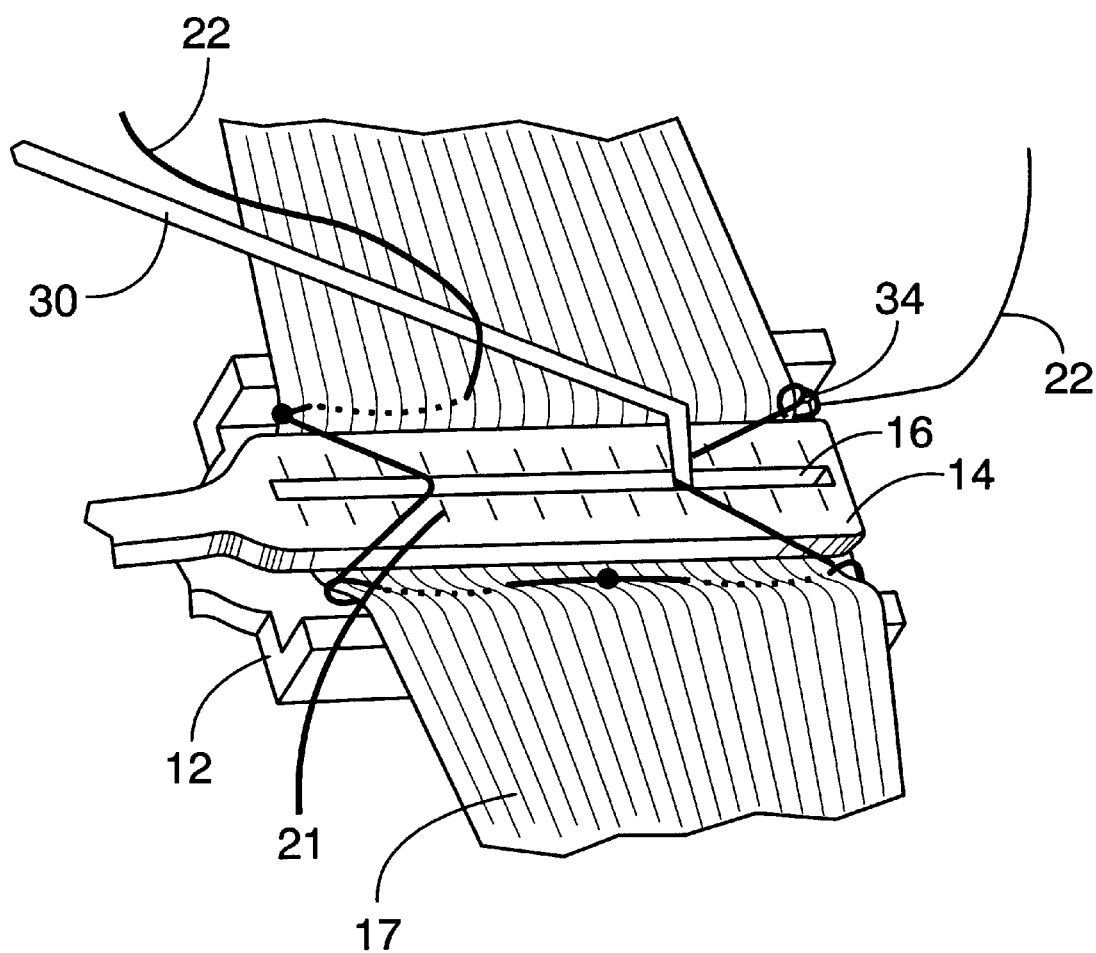
FIG. 5 is another plan view of the embodiment of the present invention illustrated in FIG. 1 illustrating the use of the present invention.

FIG. 4 illustrates the use of Clamp 10 to create the muscle recession. A fixation device 30 is used that can be either a punctal dilator, 00-lacrimal probe or other similar device well known to those of ordinary skill in the art. The fixation device 30 is placed at one of the plurality of hatch marks 21 which is the point of recession for the eye muscle. The point of recession where the fixation device 30 is placed in the particular example illustrated in FIG. 4 is approximately 4 mm. The bottom portion of FIG. 4 illustrates the geometric calculation used to determine the actual point of recession. As shown in FIG. 4, the suture 22 is brought around the fixation device 30 and back to the edge of muscle 17 where a locking bite 32 is placed. As is known to those in the surgical art, a locking bite describes a knot being placed in a suture rather than an open loop. The same procedure is then performed at the opposite edge of the muscle 17 creating another locking bite 34 as illustrated in FIG. 5.

Figure 6:
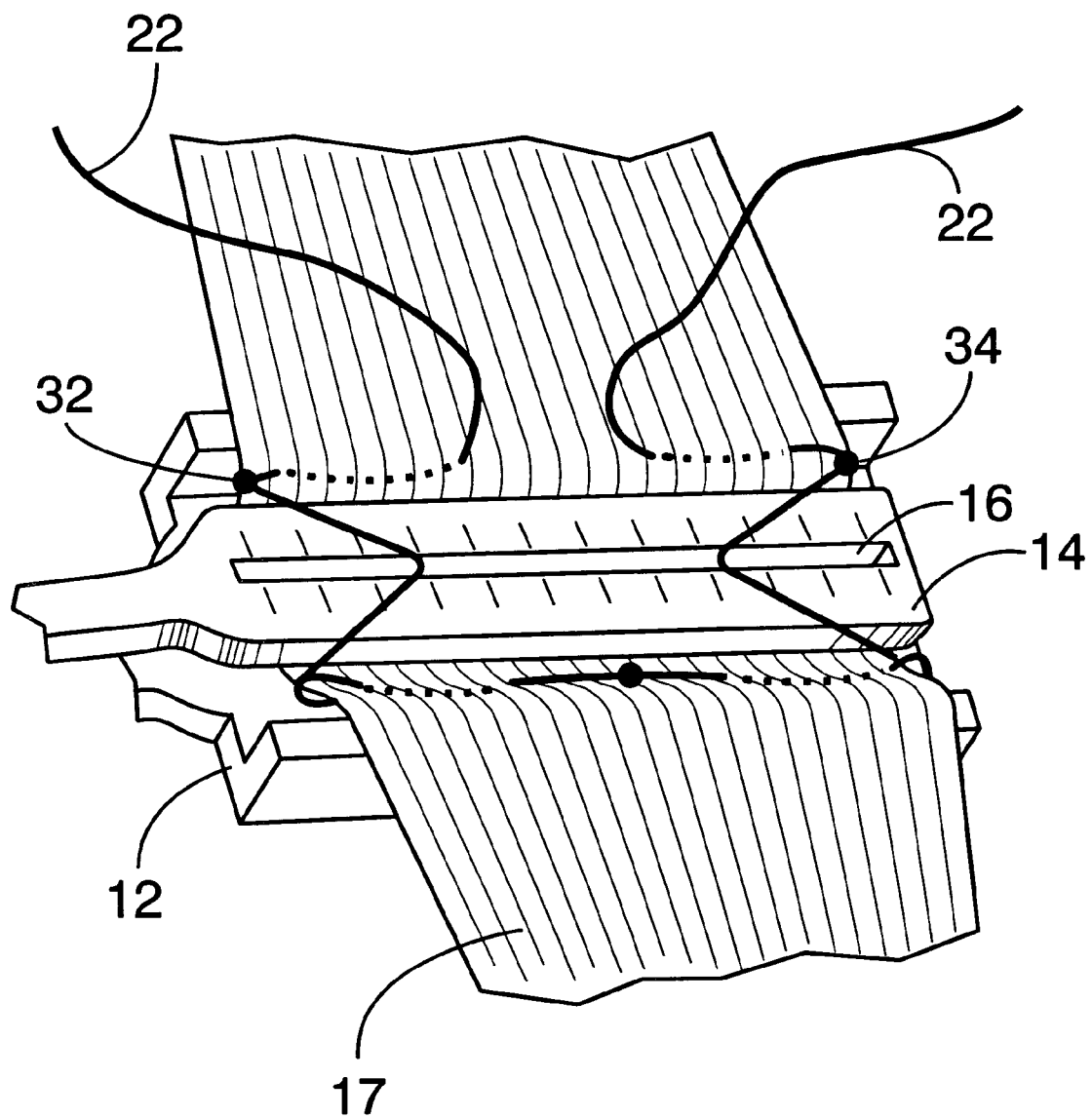
FIG. 6 is another plan view of the embodiment of the present invention illustrated in FIG. 1 illustrating the use of the present invention.

Next the sutures 22 from the locking bites 32 and 34 are passed centrally after the fixation device 30 is removed as illustrated in FIG. 6. The result is that the sutures 22 form a complete loop with the suture tied to itself.

Figure 7:
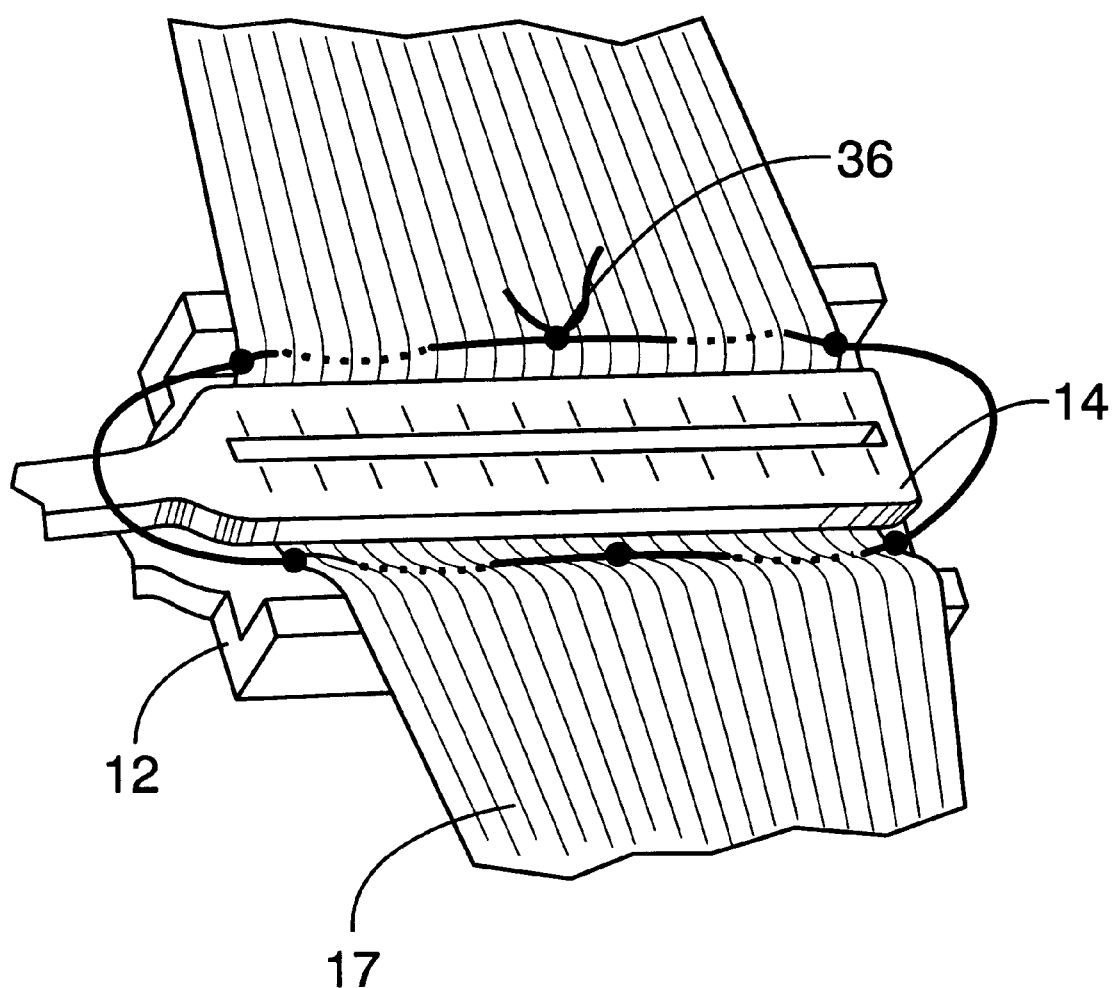
FIG. 7 is another plan view of the embodiment of the present invention illustrated in FIG. 1 illustrating the use of the present invention.

The next step in the procedure is illustrated in FIG. 7. At this point, the sutures 22 are tied together at point 36. As is known to those of ordinary skill in the art, sutures 22 have needles attached to each end. In one method of performing the surgery, the needles on the ends of the sutures 22 will be cut off at this point.

Figure 8:
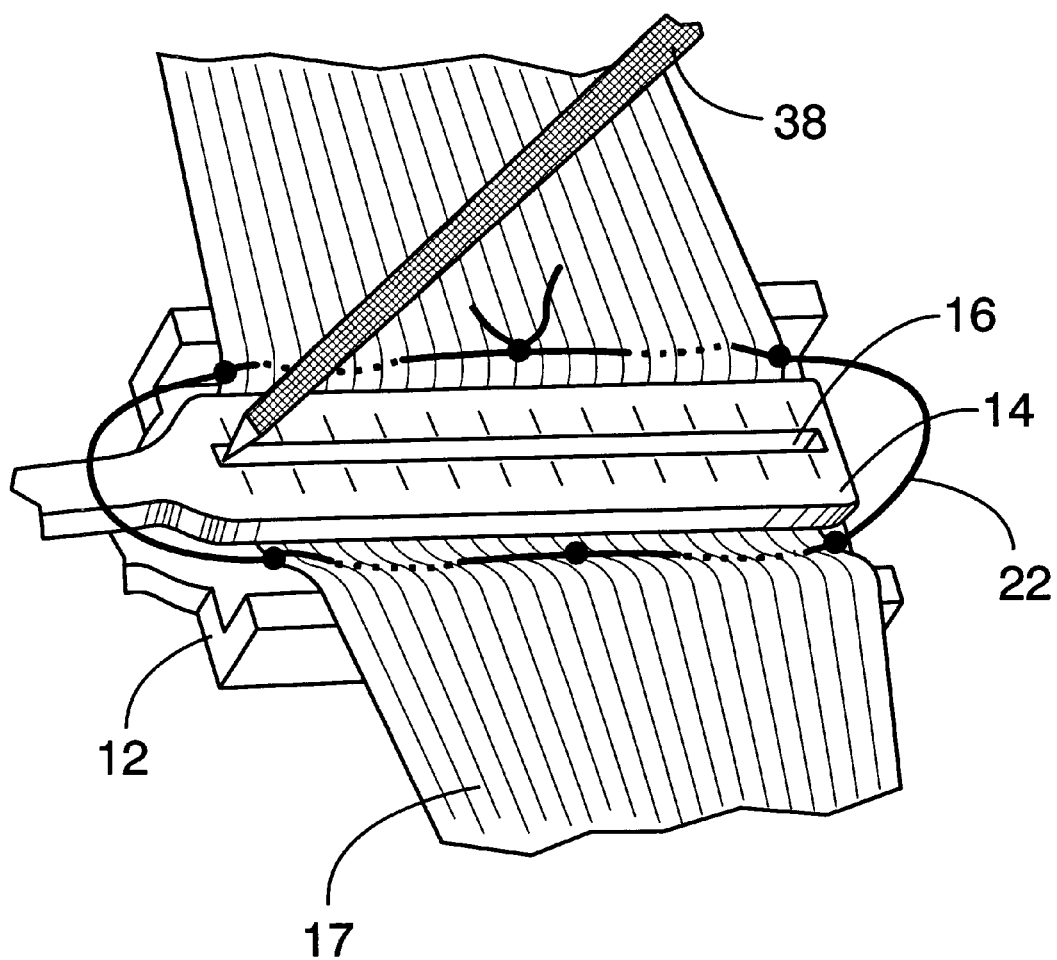
FIG. 8 is another plan view of the embodiment of the present invention illustrated in FIG. 1 illustrating the use of the present invention.

FIG. 8 illustrates the next step in the procedure which is to incise the muscle 17. A knife blade 38, preferably a super sharp, is placed within slit 16 and the muscle 17 is incised. The knife blade 38 should be sized only as long as necessary to incise the muscle 17. As can be seen the first plate 12 protects the sclera from accidental incision as the knife blade 38 incises through the muscle 17.

In the next step after the muscle 17 is incised, the first plate 12 and the second plate 14 of Clamp 10 are opened as shown in FIG. 9. When the Clamp 10 is opened, the muscle 17 falls to its recessed position. Clamp 10 is then removed from the patient. After the Clamp 10 is removed, the muscle 17B is in its recessed position and supported by the sutures 22 as shown in FIG. 10. FIG. 10 illustrates what is referred to as a complete muscle recession.

Figure 14:
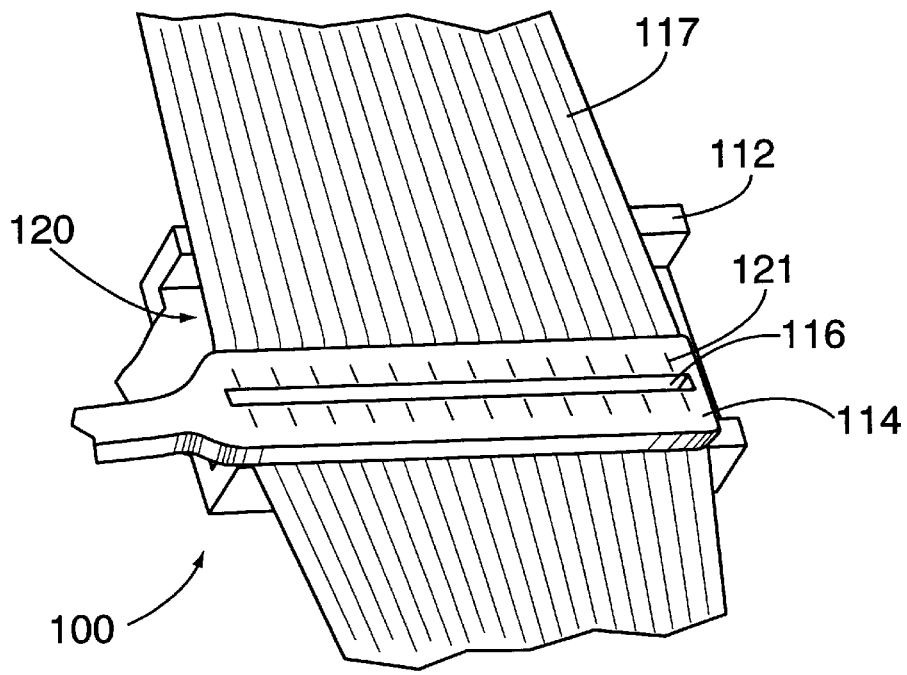
FIG. 14 is a plan view illustrating an alternative embodiment of the present invention.
Figure 14:
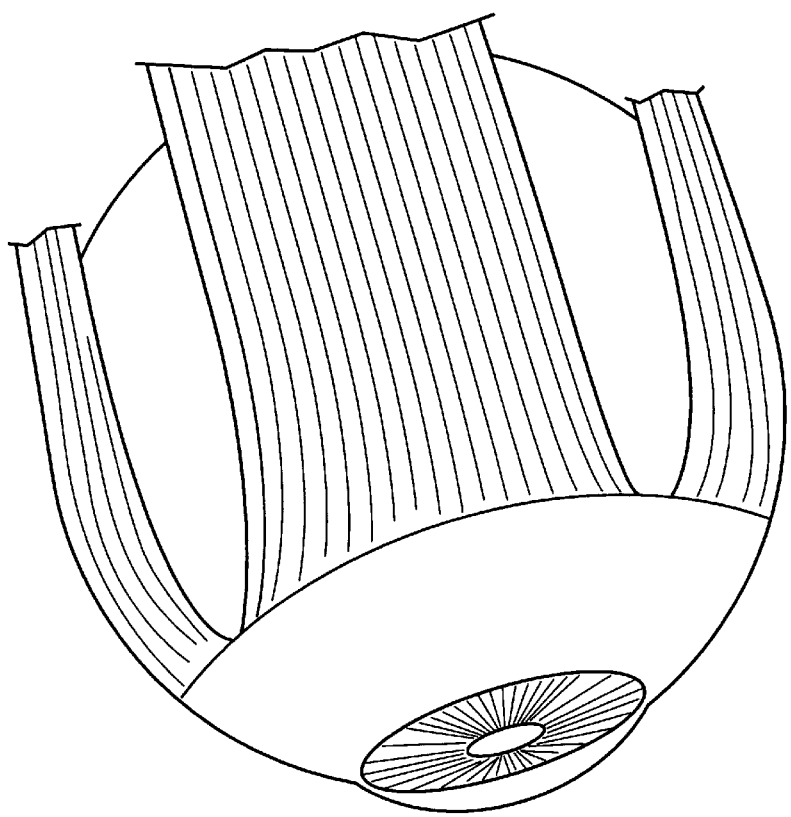

After the Clamp 10 is removed, there are several methods that can be used to stabilize and adjust the position of the muscle 17. These various options are illustrated in FIGS. 11, 12 and 13. FIG. 11 illustrates the needles still attached if the surgeon chose not to cut them as was illustrated in connection with FIG. 7. In the illustration shown in FIG. 11, the suture 22 is used to further support the muscle or to create an adjustable knot through the original insertion site 17A. FIG. 12 illustrates the use of the sutures 22 as a central support to prevent sagging of the muscle 17. The knot 40 illustrated in FIG. 12 can be tied or left as a bow knot for future adjustment. FIG. 13 illustrates a method whereby the sutures 22 are locked at the muscle edge 42 and then brought back to the insertion point, where the muscle 17 attaches to the sclera, for adjustment. This adjustment will only allow for a decrease of the recession, i.e. pulling the muscle forward FIG. 14 illustrates an alternative embodiment 100 of the Clamp 10. Clamp 100 is primarily directed for use in a second operation on the muscle or "reoperation." The Clamp 100 is comprised of a first plate 112 and a second plate 114. The second plate 114 comprises a longitudinal slit 116 and a plurality of hatch marks 121. FIG. 14 illustrates the Clamp 100 in use with a muscle 117 clamped in place. As noted above the Clamp 10 comprises two grooves 18 and 20. Clamp 100 comprises one groove 120. In reoperations, after the muscle 117 is succesfully hooked, it is difficult to pass sutures and incise the muscle without cutting the sutures. The Clamp 110 is used in a similar fashion as the Clamp 10 described above except that only the groove 120 is required.

Figure 15:
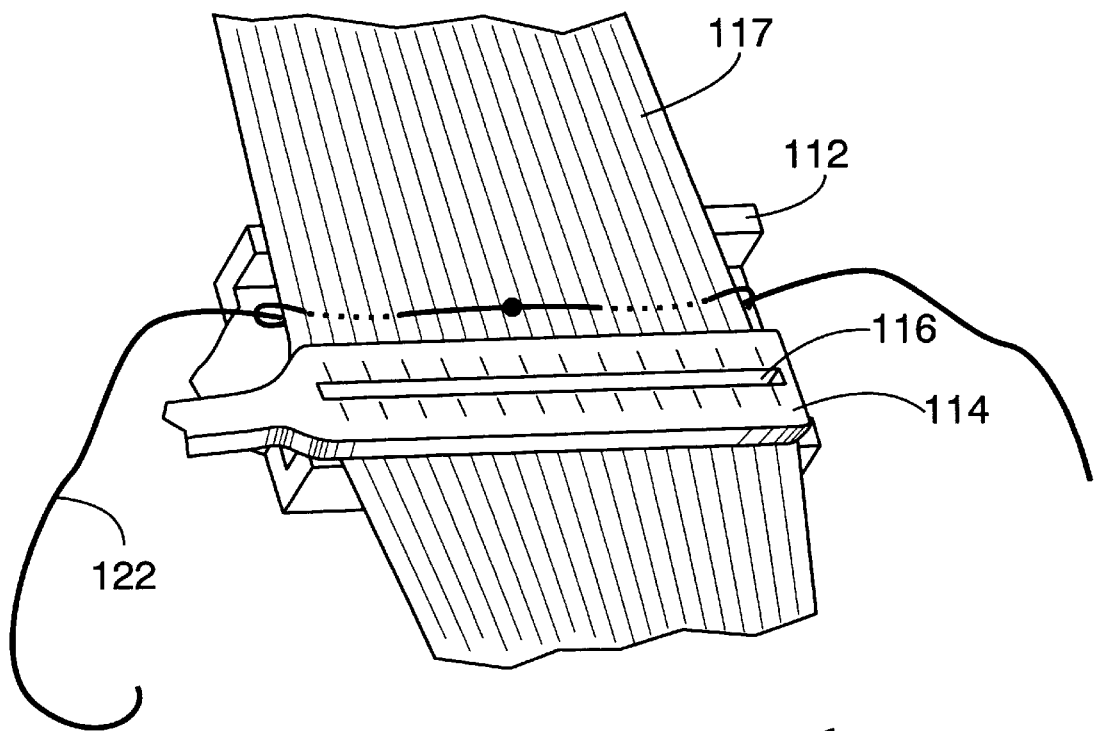
FIG. 15 is another plan view of the alternative embodiment of the present invention illustrated in FIG. 14.
Figure 15:
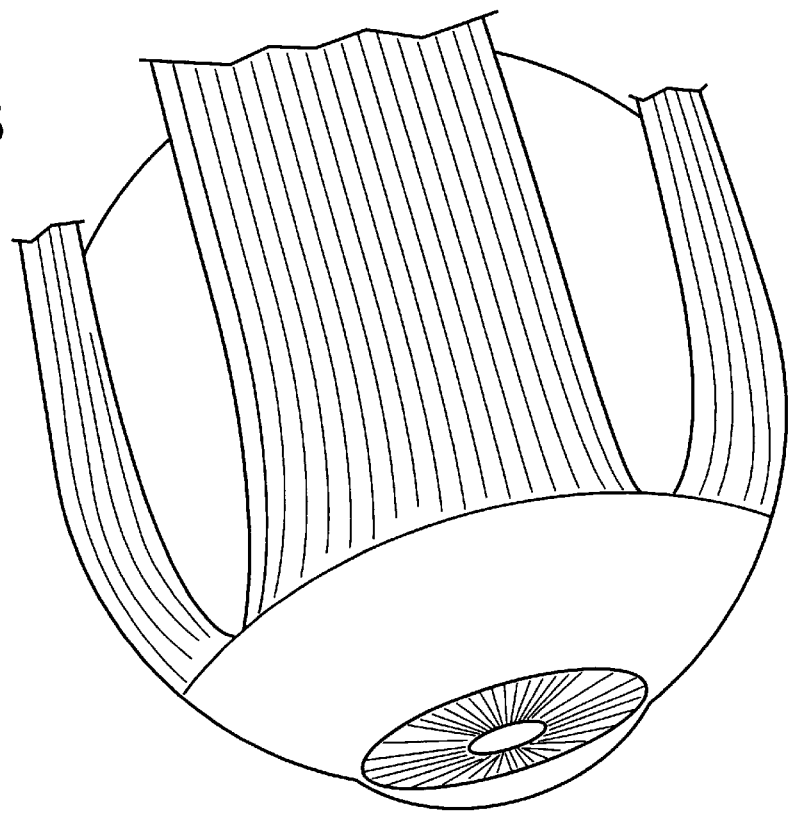

FIG. 15 illustrates the use of the Clamp 110. A suture 122 is threaded between the muscle 117 and the second plate 114 in a protected fashion in that the needle on the suture cannot perforate the sclera due to the first plate 112. The muscle 117 is incised through slit 116 in the same manner as described above in connection with FIG. 8. Again, as with the Clamp 10, the risk of cutting the sclera or the sutures 122 is minimized by use of the Clamp 110. After the muscle is incised, the muscle is reattached to the sclera in the usual0 manner known to those of ordinary skill in the art by suturing directly to the sclera.

Figure 16:
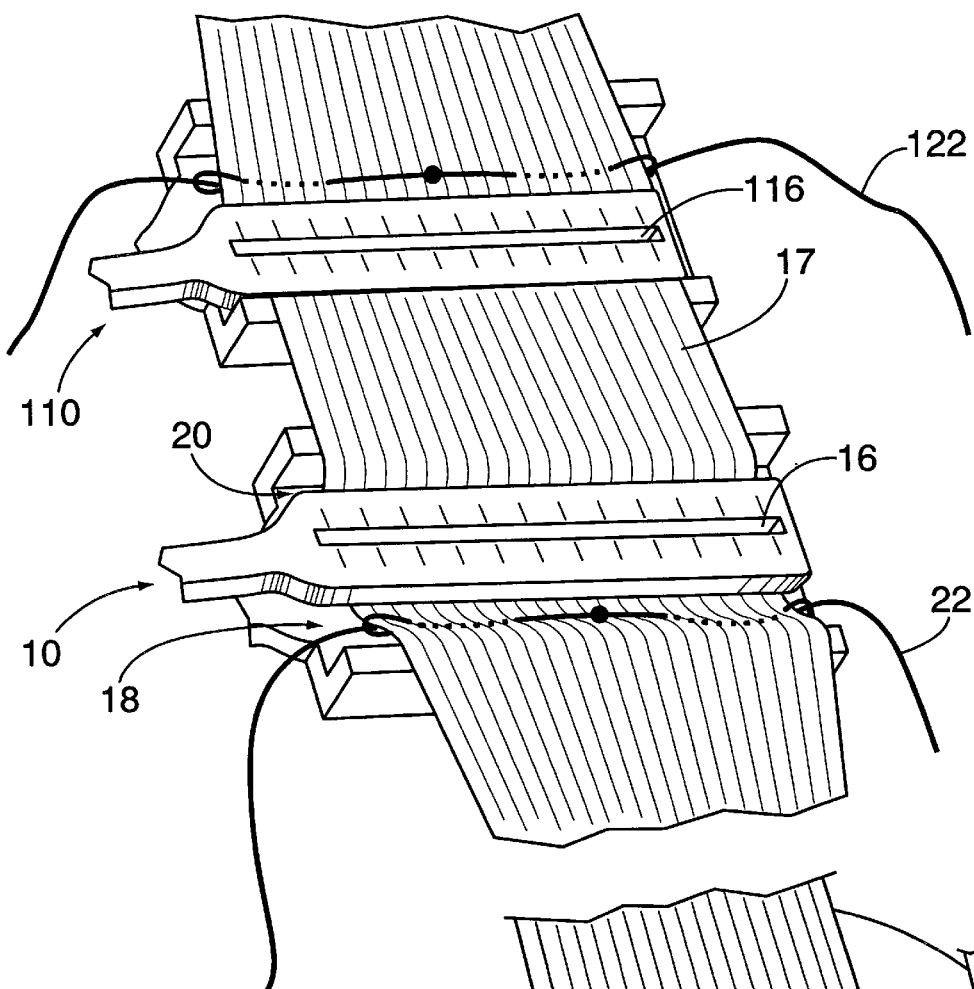
FIG. 16 is a plan view illustrating the use of the embodiment of the present invention illustrated in FIG. 1 in combination with the alternative embodiment illustrated in FIG. 14.
Figure 16:
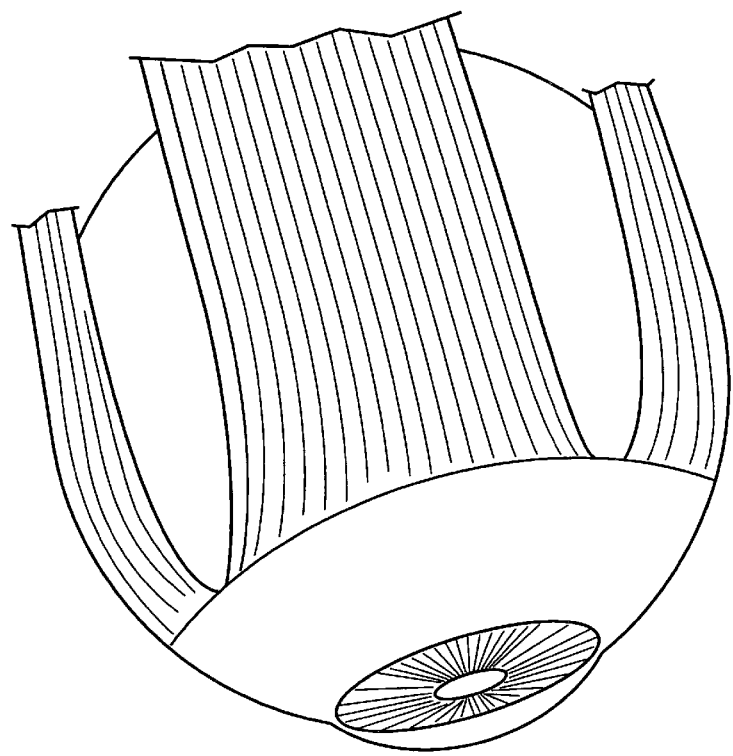

FIG. 16 illustrates the use of the Recession Clamp 10 in combination with the reoperation Clamp 110. The reoperation Clamp 110 is located and clamped at the required resection site. Use of the reoperation Clamp 110 allows for more precise placement of the suture 122. The recession Clamp 10 is located and clamped at the insertion by use of groove 18 only. The sutures 22 and 122 are placed as shown in FIG. 16 by the methods previously described. The muscle 17 between the Clamp 10 and the Clamp 110 is incised b using the slits 16 and 116. This method of using the slits 16 and 116 provides hemostasis. After incision, the muscle ends can be joined together by any of a variety of methods known to those of ordinary skill in the art.

Those of ordinary skill in the art will recognize that the embodiments just described merely illustrate the principles of the present invention. Many modifications may be made thereto without departing from the spirit and scope of the invention as set forth in the following claims.

What is claimed is:

1. A strabismus recession clamp comprising:
 a) a solid first plate comprising a top surface wherein the top surface is adapted to receive an eye muscle during a recession procedure;
 b) a second plate comprising a longitudinal slit wherein the longitudinal slit comprises a plurality of hatch marks and is adapted to receive a knife blade during the recession procedure and the second plate is adapted to be received in the top surface of the first plate after the eye muscle is received in the top surface of the first plate and thereby a first groove for initial suturing of the eye muscle is formed between the first plate and the eye muscle and a second groove for recession of the eye muscle is formed between the first plate and the eye muscle; and
 c) a locking device for securing the second plate into position over the eye muscle after the second plate is received in the top surface of the first plate.

2. A strabismus recession clamp for reoperations comprising:
 a) a solid first plate comprising a top surface wherein the top surface is adapted to receive an eye muscle during a recession procedure;
 b) a second plate comprising a longitudinal slit wherein the longitudinal slit comprises a plurality of hatch marks and is adapted to receive a knife blade during the recession procedure and the second plate is adapted to be received in the top surface of the first plate after the eye muscle is received in the top surface of the first plate and thereby a first groove for initial suturing of the eye muscle is formed between the first plate and the eye muscle; and c) a locking device for securing the second plate into position over the eye muscle after the second plate is received in the top surface of the first plate.

3. A method for performing muscle recession surgery using the strabismus recession clamp of claim 1 comprising the steps of:

a) locating the first solid plate of the strabismus recession clamp on top of the sclera on top of the sclera and the muscle at the muscle insertion;

b) placing an eye muscle on the top surface of the first solid plate of the strabismus recession clamp;

c) placing the second plate of the strabismus recession clamp onto the top of eye muscle;

d) securing the second plate into position by means of the locking device;

e) threading a double armed suture through the first groove of the second plate and then placing a central knot and two first locking bites in the double armed suture;

f) determining a point of recession for the eye muscle at one of the plurality of hatch marks on the longitudinal slit and then placing a fixation device at the point of recession in the longitudinal slit;

g) passing the double armed suture around the fixation device and back to an edge of the eye muscle wherein a second locking bite in placed in the double armed suture;

h) removing the fixation device;

i) repeating steps f and g on an opposite edge of the eye muscle;

j) tieing the ends of the double armed suture together to form a complete loop;

k) incising the eye muscle by use of a knife through the longitudinal slit in the second plate;

l) releasing the locking device and removing the second plate;

m) and adjusting the position of the eye muscle as necessary.

* * * * *